(12) United States Patent
Jung et al.

(10) Patent No.: US 9,057,680 B2
(45) Date of Patent: Jun. 16, 2015

(54) PORTABLE INDUSTRIAL LIMITED ANGLE GAMMA-RAY TOMOGRAPHY SCANNING SYSTEM

(75) Inventors: Sung-Hee Jung, Daejeon (KR); Jong-bum Kim, Daejeon (KR); Jinho Moon, Daejeon (KR)

(73) Assignees: Korea Atomic Energy Research Institute, Daejeon (KR); Korea Hydro and Nuclear Power Co., Ltd., Seoul (KR)

( * ) Notice: Subject to any disclaimer, the term of this patent is extended or adjusted under 35 U.S.C. 154(b) by 884 days.

(21) Appl. No.: 13/277,536

(22) Filed: Oct. 20, 2011

(65) Prior Publication Data

US 2012/0140876 A1 Jun. 7, 2012

(30) Foreign Application Priority Data

Dec. 2, 2010 (KR) ........................ 10-2010-0121966

(51) Int. Cl.
*G01N 23/04* (2006.01)

(52) U.S. Cl.
CPC ........ *G01N 23/046* (2013.01); *G01N 2223/419* (2013.01); *G01N 2223/612* (2013.01)

(58) Field of Classification Search
CPC .... G01N 23/046; G01N 23/18; G01N 23/185
USPC .............. 378/20, 54, 57, 58, 59, 60, 61, 146, 378/147, 11
See application file for complete search history.

(56) References Cited

U.S. PATENT DOCUMENTS

| | | | | |
|---|---|---|---|---|
| 5,420,427 A | * | 5/1995 | Morgan et al. | 250/360.1 |
| 6,940,941 B2 | * | 9/2005 | Gregerson et al. | 378/4 |
| 2004/0179647 A1 | * | 9/2004 | Zhao et al. | 378/57 |
| 2007/0206719 A1 | * | 9/2007 | Suryanarayanan et al. | 378/4 |
| 2011/0122990 A1 | * | 5/2011 | Dafni | 378/4 |

FOREIGN PATENT DOCUMENTS

| | | |
|---|---|---|
| JP | 05-018729 A | 1/1993 |
| KR | 10-0718671 B1 | 5/2007 |
| KR | 10-0863747 B1 | 10/2008 |

(Continued)

OTHER PUBLICATIONS

Kim, Jong Bum, Sung Hee Jung, Jin Ho Moon, Simulation on a Limited Angle Beam Gamma Ray Tomography, Transactions of the Korean Nuclear Society Autumn Meeting, Oct. 2010, pp. 863-864, Jeju, Korea.

*Primary Examiner* — Toan Ton
*Assistant Examiner* — Mona M Sanei
(74) *Attorney, Agent, or Firm* — Maier & Maier, PLLC

(57) ABSTRACT

Provided is a diagnostic method and system capable of applying tomography to industrial long cylindrical process systems, such as a pipe line, which are difficult to diagnose using existing medical or industrial computed tomography (CT) scanners. Existing industrial X-ray CT scanners cannot be used for such a pipe that is attached to the process system and thus cannot be placed on the turntable, and existing image diagnostic apparatuses of a fan beam type, a collimated beam type, etc. having a stereotyped structure are next to impossible to move and use for undetachable process systems and their peripheral devices. To solve these problems, there is provided a gamma-ray tomography scanning system that is capable of being directly attached to a pipe in operation and measuring a cross section of the pipe.

9 Claims, 11 Drawing Sheets

(56) References Cited

FOREIGN PATENT DOCUMENTS

| KR | 10-0880864 B1 | 1/2009 |
| KR | 10-2009-00898759 | 8/2009 |
| KR | 10-0931304 | 12/2009 |
| WO | 2009097580 A2 | 8/2009 |

\* cited by examiner

Source displacing slide
having
a detachable structure

PORTABLE INDUSTRIAL LIMITED ANGLE GAMMA-RAY TOMOGRAPHY SCANNING SYSTEM

RELATED APPLICATIONS

This application claims priority under 35 U.S.C. §119 to Korean Patent Application No.: 10-2010-0121966, filed on Dec. 2, 2010, the disclosure of which is incorporated by reference herein in its entirety.

BACKGROUND OF THE INVENTION

1. Field of the Invention

The present invention relates, in general, to a gamma-ray tomography scanning system and, more particularly, to a diagnostic method and system capable of applying tomography to industrial long cylindrical process systems, such as a pipeline, which are difficult to diagnose using existing medical or industrial computed tomography scanners.

2. Description of the Related Art

In general, computed tomography (CT) scanners (or computed tomographs) have been used in various fields such as industrial fields and the medical field.

CT scanners are machines that allow information about a cross-sectional view of a substance or a status of tissue, which cannot be obtained by conventional X-ray apparatuses, to be realized as an image. The CT scanner was commercialized with the invention by G. Hounsfield in 1971, and is designed to be able to observe each cross-sectional tomogram of an object to using a technique that combines images, which are obtained by penetrating X-rays into the object to be scanned at various angles, into a three-dimensional image.

One example of the conventional CT scanner is disclosed in Korean Registered Patent No. 10-0880864 (registered on Jan. 21, 2009), entitled "Nano-Scale X-ray Computed Tomography Scanner."

In detail, the CT scanner disclosed in Korean Registered Patent No. 10-0880864 furnishes a nano-scale high-definition image using X-ray generating means having a focus size of 1 micrometer or less, in order to solve a problem, namely that although biological medical X-ray CT scanners have been used more and more with recent developments in the bio-industry and bio-engineering, they have run up against a limit because they have furnished a micro-scale definition image and thus have not been widely applied to various studies of a bio-engineering field.

Further, existing CT scanners extract a part of tissue, fix the extracted tissue to a holder, and test the extracted tissue. Since the extracted tissue is transformed into dead tissue after a predetermined time, the extracted tissue is scanned only for a short time and it is very difficult to obtain a clear image from the extracted tissue. Moreover, it is difficult for existing CT scanners to scan the tissue because of the deformation or contamination of the tissue during examination. To solve these problems, the CT scanner disclosed in Korean Registered Patent No. 10-0880864 significantly increases the test time of a biological specimen by providing cooling means to a holder fixing the specimen so as to continuously protect the specimen fixed to the holder from X-rays.

Further, another example of the conventional CT scanner is disclosed in Korean Registered Patent No. 10-0718671 (registered on May 9, 2007), entitled "X-ray Cone Beam CT Scanner Having 2-Dimensional Reference Detector and Collimator for Reference Detector."

In detail, in order to solve a problem of existing X-ray CT scanners to which a 2-dimensional detector is applied, and in order to prevent spatial resolution from being reduced when reconstructing a 2-dimensional tomogram only when information about spatial displacement of an X-ray focus caused by irregular movement of the X-ray focus should be obtained with respect to all of X, Y, and Z axes, the CT scanner disclosed Korean Registered Patent No. 10-0718671 enhances the spatial resolution to observe a finer structure of a subject by applying a 2-dimensional detector as a reference detector instead of a one-dimensional detector, acquiring irregular movement of a X-ray tube focus over time for each view in three dimensions of X, Y, and Z axes, and reflecting the acquired information during a process of reconstructing a tomogram.

Further, another example of the conventional CT scanner is disclosed in Korean Registered Patent No. 10-0863747 (registered on Oct. 9, 2008), entitled "Apparatus for Computerized Tomography Having Pair of Synchronized Gantries."

In detail, when X-ray tomography scanning is required to check a surgical process or the state of a lesion of a patient who is undergoing an operation, the patient should be transferred to a tomography scanning room in order to obtain a tomogram. However, various external measurement instruments, a surgical instrument, a gas and blood feeder, etc. are connected to the patient, and thus it is difficult to transfer the patient. For this reason, it is difficult to obtain the tomogram using a conventional CT scanner. Further, although the conventional CT scanner is applied to the patient undergoing an operation, the patient is located in a gantry when scanned by the CT scanner, and thus it is impossible to check the state of the patient. Moreover, the conventional CT scanner has an X-ray source and an X-ray detector mounted in one gantry, and the gantry has considerable weight. As such, it is difficult to rotate the gantry at a high speed using one driving motor. When an organ such as a heart showing continuous movement at a rapid speed is scanned, it is difficult to obtain a clear tomogram. This may cause a diagnostic error. To solve these problems, the CT scanner disclosed Korean Registered Patent No. 10-0863747 is configured to secure a space capable of treating a patient by mounting an X-ray source and an X-ray detector on a pair of gantries spaced apart from each other by a predetermined distance respectively, thereby permitting X-ray tomography scanning during an operation or treatment, and to obtain a clearer tomogram of an organ moving at a high speed by allowing each gantry to rotate at a high speed, thereby making it possible to prevent a diagnostic error.

In addition, another example of the conventional CT scanner is disclosed in Korean Registered Patent No. 10-0931304 (registered on Dec. 3, 2009), entitled "Industrial Tomography Device Using Gamma-Ray Source."

In detail, since most existing X-ray CT scanners are intended to be used on a human body, radiation exposure and structure thereof are optimized to the human body, and thus these X-ray CT scanners are rarely used for industrial purposes. It is difficult to apply Magnetic Resonance Imagers (MRIs) to objects made of, for instance, metal. It is difficult for existing industrial X-ray CT scanners to diagnose objects having a high attenuation coefficient. Usually, industrial X-ray CT scanners are designed to rotate and scan small objects on a turntable. Consequently, since the industrial X-ray CT scanners are small CT scanners for scanning parts using the turntable, they cannot perform tomography scanning on a fixed object such as a pipe attached to facilities or a reactor.

Meanwhile, since the reactor or pipe of the industrial facilities is mostly formed of metal, it is difficult to use the X-ray CT. Even in the case of a small pipe on which X-ray CT inspection can be performed, the pipe must inevitably be separated from the facilities to perform the X-ray CT inspection. However, if to do so, there is the problem of a tremendous loss being caused by process shutdown. Due to this problem, there is a demand for a technique capable of finding out the cause of an internal abnormal phenomenon by measuring cross sections of various reactors and pipes during their operation in refineries and petrochemical industry.

However, the CT scanner of the related art has a problem in that the density and size of the object are restricted due to the use of X-rays. To solve this problem, a CT scanner using high-energy gamma rays has been developed. In this gamma-ray CT scanner, a relatively large detector is used to enhance the detection efficiency. Thus, when it compared to X-ray CT, the gamma-ray CT scanner generally obtains low resolution image from two-dimensional scanning with one-dimensional arrangement of the detector.

That is, in the case of the CT scanner that performs tomography or measurement using the one-dimensional arrangement of the detector, an apparatus designed to move up and down a subject when changing a cross section must be separately provided. This structure is restricted to large subjects.

Thus, to solve these problems, the CT scanner disclosed in Korean Registered Patent No. 10-0931394 includes: an optical system having an annular rotator into which a subject is inserted and which is allowed to be rotated left and right, a gamma-ray collimator coupled to the rotator, and a radiation detector disposed so as to face the gamma-ray collimator; and a driver installed outside the optical system so as to move up and down the optical system, whereby the restriction in size of a detectable subject and the change of a cross section of the subject is eliminated by moving up and down the optical system, and the subject is easily inspected by allowing the optical system to be rotated left and right.

As described above, conventional CT scanners generally include an X-ray generator, a mechanism for rotating a subject, and a detector. The object is disposed between the X-ray generator and the detector, and X-rays are applied in a cross-sectional direction of the object at various positions. In X-ray CT scanners, attenuation of X-rays by different attenuation coefficient of substances is measured as data from different directions, and the data is converted into a cross-sectional image by mathematical operations using a computer. Thereby, the cross-sectional image corresponding to a scanned area of the subject is reconstructed and shown.

Further, these CT scanners are divided into medical and industrial CT scanners according to the kind of the subject, the observation area of the subject, and the purpose of scanning the subject.

The existing industrial X-ray CT scanners provide high-definition results, but they can measure only an object such as a disassembled part that can be placed on the turntable. For this reason, industrial X-ray CT scanners have the drawback of not being able to be used for, for instance, a pipe-line that is attached to a process system and thus is not able to be placed on the turntable.

Further, the existing image diagnostic apparatuses of the fan beam type, the collimated beam type, etc. having a stereotyped structure are next to impossible to move and use for undetachable process systems and their peripheral units.

That is, since the typical industrial X-ray CT scanners perform tomography scanning on a detachable object using a turntable, they cannot measure an undetachable object. There are many undetachable objects such as industrial process. The demand of tomography scanning for industrial process is increasing but conventional CTs cannot be applied for industrial process. It is preferable to provide a commercialized CT scanner that can be substantially applied to these objects. However, no CT scanner that meets all requirements has been provided up to now.

SUMMARY OF THE INVENTION

Accordingly, the present invention has been made keeping in mind the above problems of the related art, where the conventional tomography apparatuses, which have a stereotyped gantries, are next to impossible to move and use for undetachable process systems and their peripheral devices. Thus, an objective of the present invention is to provide a gamma-ray tomography scanning system that is capable of being directly attached to, and measuring a cross section of the industrial system during their operation.

In order to achieve the above objective, according to one aspect of the present invention, there is provided a portable industrial limited angle gamma-ray tomography scanning system, which includes: a scanning part for tomography scanning; and a clamping part for attaching the scanning part to an object to be measured.

Here, the scanning part may include: a source assembly emitting radiation; driving device to rotate the source assembly and a detector assembly detecting the radiation from gamma-ray source.

Further, the detector assembly may be configured to be fixed, and the source assembly may be configured to be moved.

Furthermore, the source assembly may include: a source moving slide that is displaced along the base plate; a source moving track that is coupled to the source moving slide; and a source collimator that is coupled to the source moving track;

Furthermore the driving device may include: a motor and a gear that displace the source assembly.

Here, the source moving track may include teeth formed on a lateral face thereof so as to be engaged with the gear. Thus, when the motor is driven to rotate the gear, the source collimator is displaced along the source moving track.

Further, the source moving slide coupled to the base plate may be configured to have a detachable structure.

Meanwhile, the detector assembly may be configured so that at least one detecting unit is arranged in a circular arc shape.

Here, the detecting unit may employ a CsI gamma-ray detecting unit.

The source assembly may employ a sealed gamma-ray source, and be configured to use $^{137}Cs$ or $^{60}Co$ as a radioactive isotope that emits gamma rays.

The clamping part may be manufactured depending on a size of the object to be measured. Thus, measurements are possible for objects having various sizes.

The portable industrial limited angle gamma-ray tomography scanning system may further include an image reconstructing part that performs cross-sectional reconstruction using an image reconstruction program for the cross-sectional reconstruction of limited angle data on the basis of measured data.

Here, the image reconstruction program may be configured to use an iterative algorithm such as the maximum likelihood-expectation maximization (ML-EM) algorithm, a total variation (TV) algorithm, or an algebraic reconstruction technique (ART) algorithm.

According to another aspect of the present invention, there is provided a tomography scanning method using a portable industrial limited angle gamma-ray tomography scanning system. The tomography scanning method includes the steps of: scanning an object to be measured using the portable industrial limited angle gamma-ray tomography scanning system; and performing image reconstruction using an image reconstruction program on the basis of data that is measured using the portable industrial limited angle gamma-ray tomography scanning system in the scanning step.

Here, the image reconstruction program may be configured to use an iterative algorithm such as an ML-EM algorithm, a TV algorithm, or an ART algorithm.

According to yet another aspect of the present invention, there is provided a portable industrial limited angle gamma-ray tomography scanning system, which includes: a scanning part for tomography scanning; a clamping part for attaching the scanning part to an object to be measured; and an image reconstructing part for performing cross-sectional reconstruction using an image reconstruction program on the basis of measured data.

Here, the scanning part may include: a source assembly generating radiation; driving device rotating the source assembly; and a detector assembly detecting the radiation generated from the source assembly.

Further, the detector assembly may be configured to be fixed, and the radiation generator may be configured to be displaced.

The source assembly may include: a source moving slide that is coupled to the base plate; a source moving track that is disposed on the source moving slide; and a source collimator that is displaced along the source moving track.

Furthermore, driving device may include; and a motor and a gear that displace the source assembly.

Here, the source moving track may include teeth formed on a lateral face thereof so as to be engaged with the gear. Thereby, when the motor is driven to rotate the gear, the source collimator is displaced along the source moving track.

Further, the source moving slide coupled to the base plate may be configured to have a detachable structure.

Meanwhile, the detector assembly may be configured so that at least one detecting unit is arranged in a circular arc shape.

Here, the detecting unit may employ a CsI gamma-ray detecting unit.

The source assembly may employ a sealed gamma-ray source, and be configured to use $^{137}$Cs or $^{60}$Co as a radioactive isotope that emits gamma rays.

Further, the clamping part may be manufactured depending on a size of the object to be measured. Thereby, measurement is possible for objects of various sizes.

The image reconstruction program may be configured to use an iterative algorithm such as an ML-EM algorithm, a TV algorithm, or an ART algorithm.

According to still yet another aspect of the present invention, there is provided a tomography scanning method using a portable industrial limited angle gamma-ray tomography scanning system, which includes the measurement step using the portable industrial limited angle gamma-ray tomography scanning system.

According to the present invention as described above, the portable industrial limited angle gamma-ray tomography scanning system can be directly attached to a pipe that is in operation to measure a cross section of the pipe.

In detail, the portable industrial limited angle gamma-ray tomography scanning system includes a tomography scanning apparatus and a clamping apparatus for attaching the tomography scanning apparatus to an object to be measured. The tomography scanning apparatus is configured so that a detector assembly is fixed and a source assembly is displaced in order to reduce a measurement time.

Thus, the portable industrial limited angle gamma-ray tomography scanning system can be installed on a pipe, a reactor, or the like, which is in operation, using the tomography scanning apparatus having the aforementioned structure, wherein a gamma-ray source is displaced to measure at predetermined intervals, and penetrated gamma rays are measured and recorded at a position of the gamma-ray source by all detecting units. When the rotation of the gamma-ray source around the object has finished, the acquisition of data for the tomography scanning is terminated.

Further, the data measured in this method does not have data of a specific range of angles (i.e. limited angle data), compared to typical tomography scanning. For this reason, the portable industrial limited angle gamma-ray tomography scanning system employs an image reconstruction program to perform cross-sectional reconstruction using an iterative algorithm such as maximum likelihood-expectation maximization (ML-EM), total variation (TV), or algebraic reconstruction technique (ART) that have been known as being suitable for the cross-sectional reconstruction of limited angle data.

Accordingly, the portable industrial limited angle gamma-ray tomography scanning system can relieve the burden of separation, reassembly, etc. of the apparatus for attaching the tomography scanning system at a measurement position, reduce the measurement time by miniaturizing the source assembly and displacing the source, and be advantageous in constructing a portable system compared to the related art.

That is, the portable industrial limited angle gamma-ray tomography scanning system can provide information about the measurement of the cross section that cannot be performed by existing measurement techniques, reduce the measurement time, and be widely applied to the industrial field where pipes and their equivalents need to be diagnosed.

BRIEF DESCRIPTION OF THE DRAWINGS

The above and other objectives, features and advantages of the present invention will be more clearly understood from the following detailed description when taken in conjunction with the accompanying drawings, in which.

DETAILED DESCRIPTION OF THE INVENTION

Figure 1:
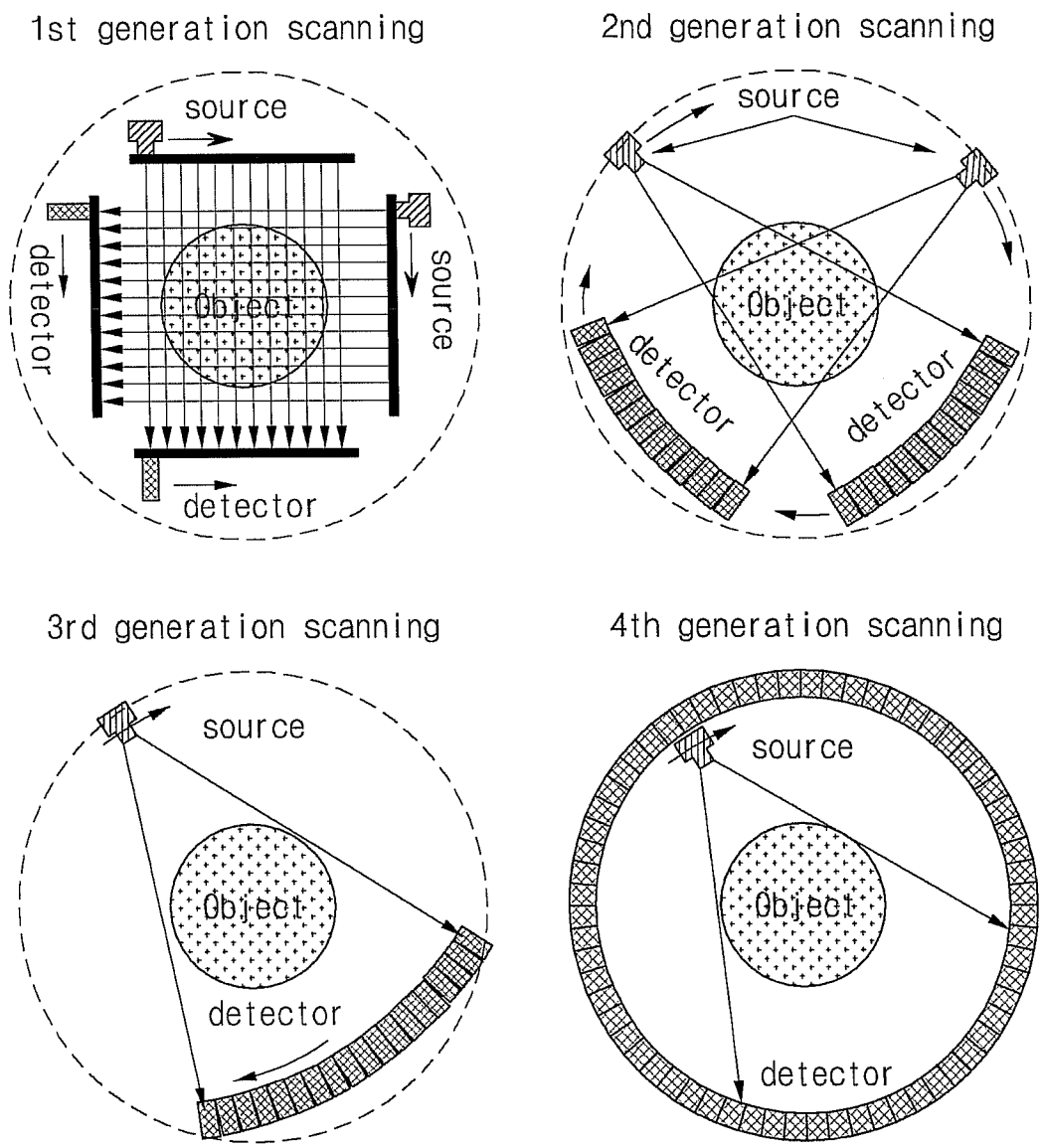
FIG. 1 is a diagram for explaining the structural classification of conventional computed tomography (CT) scanners.

Hereinafter, a portable industrial limited angle gamma-ray tomography scanning system according to an exemplary embodiment of the invention will be described in greater detail with reference to the accompanying drawings.

In the following description, it is to be noted that the exemplary embodiment is merely one embodiment for carrying out the present invention and thus the present invention is not limited to this embodiment.

As described below, the present invention provides a portable industrial limited angle gamma-ray tomography scanning system that includes an apparatus for tomography scanning and a clamping apparatus for attaching the tomography scanning apparatus to an object to be measured. Here, the tomography scanning apparatus is configured to fix a detector assembly and rotate a source assembly in order to reduce the measurement time.

Further, a space for insertion around a pipe is required so that the tomography scanning apparatus is directly attached to the pipe that is in operation. To this end, radiation detecting units of the detector are configured to be uniformly arranged in a space excluding a portion for insertion around an object. The overall arrangement of the radiation detecting units is similar to a C-shaped arrangement.

Furthermore, the source assembly employs a sealed gamma-ray source. The sealed gamma-ray source is movably attached to a C-shaped unit located inside a circular arc of the C-shaped detector.

As a radioactive isotope that emits gamma rays, $^{137}$Cs or $^{60}$Co may be used. The circular arc of the C-shaped detector and an open side of the C-shaped unit that displaces the gamma-ray source are matched with each other in the same direction, are inserted around an object such as a pipe, and are attached to the clamping apparatus installed in advance.

Thus, the tomography scanning system can be installed on a pipe, a reactor, or the like, which is in operation, using the tomography scanning apparatus having this structure, and the gamma-ray source is displaced for measurement by a predetermined interval. Penetrated gamma rays are measured and recorded at a position of the gamma-ray source by all the detecting units. When the rotation of the gamma-ray source around the reactor is completed, the acquisition of data for the tomography scanning is terminated.

Further, the gamma-ray source is displaced in such a manner that a circular arc "C" formed by the movement of the gamma-ray source faces the circular arc "C" of the detector. The data measured in this method does not have data at a specific range of angles (i.e. limited angle data), compared to typical tomography scanning.

For this reason, the present invention employs an algorithm suitable for an image reconstruction program to perform cross-sectional reconstruction on the limited angle data. That is, the cross-sectional reconstruction is performed using an iterative algorithm such as maximum likelihood-expectation maximization (ML-EM), total variation (TV), or algebraic reconstruction technique (ART) that have been known as being suitable for the image reconstruction of the limited angle data.

The current diagnosis of an industrial pipeline is made by gamma-ray radiography, gamma scan, or the like. However, since the diagnostic results are not information about the tomography scanning, they may lead to ambiguous results depending on the profile of a deposit inside the pipe.

Here, the gamma-ray radiography has the drawbacks that an imaging plate is limited in size and that the measurement time is long.

In contrast, the portable industrial limited angle gamma-ray tomography scanning system according to the exemplary embodiment of the invention can not only provide information about a cross-sectional measurement which cannot be provided by existing measurement techniques but also reduces the measurement time, so that it can be widely applied to industrial fields in which the diagnosis of pipes and their equivalents is required.

Subsequently, the portable industrial limited angle gamma-ray tomography scanning system according to the exemplary embodiment of the invention will be described in greater detail with reference to the drawings.

First, the structural classification of conventional computed tomography (CT) scanners will be described in detail with reference to FIG. 1.

Referring to FIG. 1, types of conventional CT scanners are schematically shown.

As shown in FIG. 1, a first-generation CT scanner is a commercial CT scanner from EMI which was first developed by Hounsfield.

In greater detail, the first-generation CT scanner uses one X-ray source and one detector, and alternately performs horizontal movement and rotation of the X-ray source and the detector.

Thus, since the first-generation CT scanner uses one X-ray source and one detector, it has the drawback of a long measurement time being required.

Further, a second-generation CT scanner is also called a small angle fan beam CT scanner. This small angle fan beam CT scanner reduces the measurement time compared to the first-generation CT scanner due to the use of several detectors.

However, the second-generation CT scanner has a problem in that the detectors are required to undergo horizontal movement due to a detector angle that does not completely cover an object.

In contrast, a third-generation CT scanner is called a fan beam CT scanner due to its shape, and is configured so that a beam emitted from a source to detectors in a circular arc shape completely covers an object.

The third-generation CT scanner has the advantage that only rotation of the source and the detectors is required for data measurement without requiring horizontal movement, but it has a problem in that a drift phenomenon of the detectors takes place.

Further, a fourth-generation CT scanner is configured to mount detectors in a fixed ring shape and to rotate a source.

The fourth-generation CT scanner has the advantage that it can avoid the detector drift phenomenon occurring at the third-generation CT scanner, but it has the disadvantage of increased cost due to the use of numerous detectors.

Further, medical CT scanners are different from industrial CT scanners because the objects they measure are different from each other. This difference leads to modification of gantries, a difference in the radiation energy that is used, and so forth.

The medical CT scanners mainly make use of energy of about 120 KeV and a three- or fourth-generation measurement structure, whereas the industrial CT scanners make use of various kinds of energy ranging from 30 KeV to 10 MeV, and various gentries for a collimated beam, a fan beam, a cone beam, and so on.

The industrial CT scanners also use X-rays from a linear accelerator in order to measure a specimen of high density.

Since the typical industrial CT scanners are designed to scan a detachable object using a turntable, they cannot measure an undetachable object.

Nevertheless, in the industrial field, there are many objects such as a process reactor, pipe line, etc. that are undetachable and need to be scanned. However, the tomography scanning system that can be applied to these objects has not yet been intensively developed.

According to a recent case, pipes have been experimentally measured using a first-generation gamma-ray CT scanner in Indonesia, Malaysia, Vietnam, and so forth.

The first-generation CT scanner using gamma rays has good portability due to the use of a gamma-ray source and the drivability by simple mechanical equipment, but it has a long measurement time. The measurement time is dependent upon the intensity of a source and a type of detector, but it is typically several hours or more.

In contrast, industrial process equipment has recently been measured using a third-generation gamma-ray imaging apparatus in the USA by way of experiment. In detail, several 2-inch detectors and lead shields have been temporarily installed for the purpose of measurement. In this case, the third-generation gamma-ray imaging apparatus has been temporarily constructed and used for specific process equipment, and thus has not been used for general process equipment.

A measurement case applied to a real process using the gamma-ray imaging apparatus as mentioned above is sometimes reported. However, there are many problems in putting an existing measurement apparatus into practical use.

Merits and demerits of the conventional tomography scanners as mentioned above are shown in Table 1 below.

TABLE 1

[Features of conventional CT scanner]

| Industrial CT Scanner | Merit | Demerit |
| --- | --- | --- |
| Industrial X-Ray CT Scanner | High-resolution results | Difficulty of mobile use |
| $1^{st}$-generation Gamma-Ray Scanner | Good mobility | Long measurement time |
| $3^{rd}$-generation Gamma-Ray Scanner | Short measurement time | Difficulty of mobile use |

Now, the detailed configuration of the portable industrial limited angle gamma-ray tomography scanning system according to the exemplary embodiment of the invention will be described.

As described above, for the on-site application of the tomography scanning system, the tomography scanning system is required to have high mobility and a short measurement time.

To develop the gamma-ray imaging apparatus having these characteristics, the inventors of the present invention have applied a limited angle beam tomography technique to a gamma-ray CT scanner.

Originally, the limited angle beam tomography technique was developed as a high-speed cardiac X-ray CT scanner. This technique performs measurement for limited projection data of CT measurement is performed, and then reconstructs an image from the data.

The medical or industrial X-ray CT scanner makes use of limited angle CT for the high-speed measurement of a heart, the flow of fluid, or the like, and displaces a focal point of electron beam at high speed using a bending magnet.

However, due to the structure of a target ring for maintaining a vacuum and producing bremsstrahlung radiation, a locus of the movement of the focal point does not cover the entire area of 360 degrees.

Further, since this apparatus requires an X-ray generator, a bending magnet, a controller, a vacuum chamber, and so forth, the radiation generator becomes very voluminous.

However, since the gamma-ray tomography scanning system uses a gamma-ray source, a radiation generation part becomes very simple. Since the gamma-ray tomography scanning system also uses a limited angle, it can be designed into a structure capable of inserting an object to be measured.

Further, since the gamma-ray tomography scanning system uses a gantry designed to fix detectors and to displace a source, it can reduce the measurement time.

That is, the overall configuration of the detectors and the source of the portable industrial limited angle gamma-ray tomography scanning system according to the exemplary embodiment of the invention is similar to that of the $4^{th}$-generation CT scanner, one side of which is open.

In detail, it is possible to insert an object toward the open side. Particularly, the scanner can be installed in such a manner that it is fitted around an undetachable object such as a industrial pipe line, a pillar-like structure or the like.

Here, to couple the scanner to the object to be measured, a clamping apparatus connecting the scanner and the object is required.

That is, since the scanner has a structure in which one side is open, it is more advantageous to use a separate clamping apparatus than to attach the scanner itself to the object.

Further, since the clamping apparatus is manufactured depending on the size of the pipe, measurement is possible for pipes of various sizes.

Here, data measured in the abovementioned method is a type where data of a specific range of angles is not present compared to that of a typical tomography scanner.

Thus, the present invention performs cross-sectional reconstruction using an image reconstruction algorithm, suitable for the cross-sectional reconstruction of this limited angle data.

Here, the cross-sectional reconstruction is performed using an iterative algorithm such as ML-EM, TV, or ART that have been known as being good for the image reconstruction of limited angle data.

Subsequently, the detailed configuration of the portable industrial limited angle gamma-ray tomography scanning system 20 according to the exemplary embodiment of the invention will be described with reference to FIGS. 2 to 4.

Figure 2:
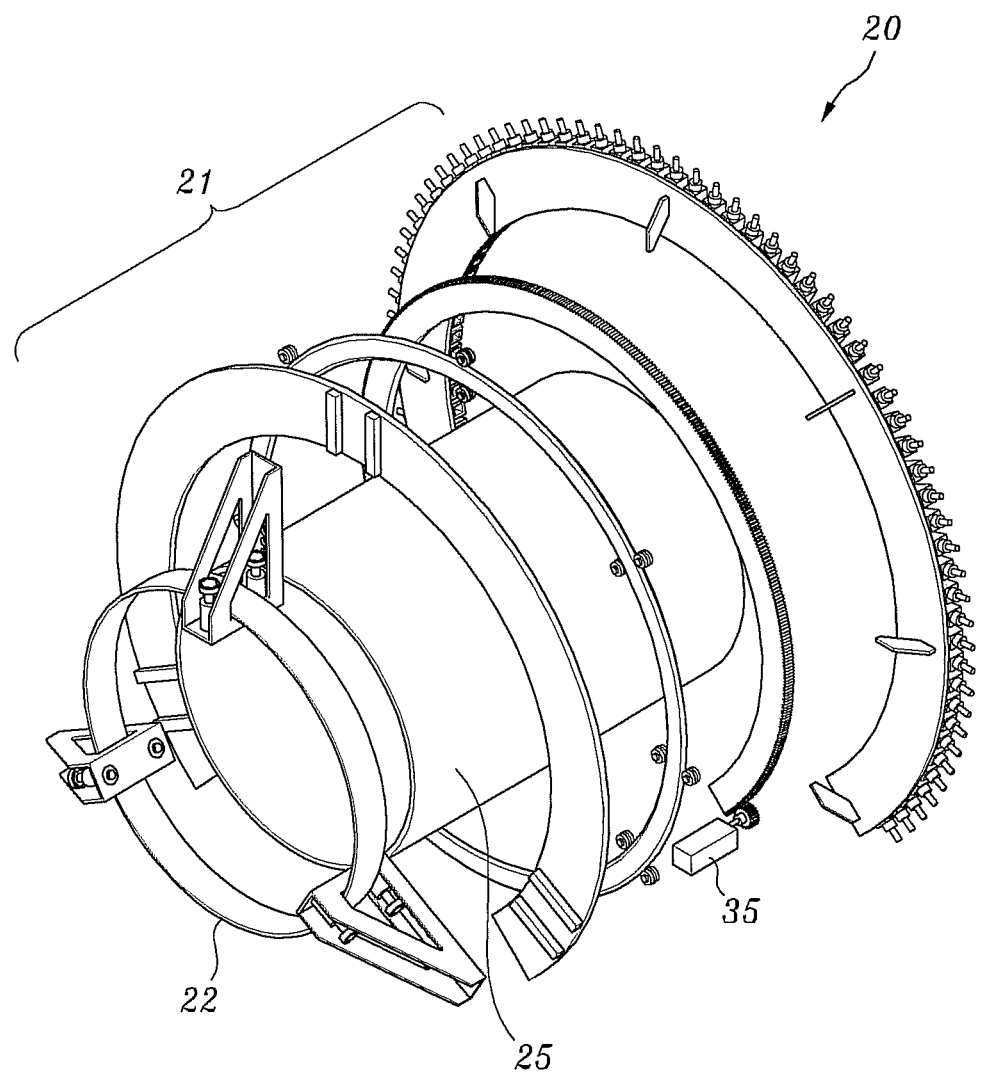
FIG. 2 is a perspective view showing the detailed configuration of a portable industrial limited angle gamma-ray tomography scanning system according to an exemplary embodiment of the present invention.
Figure 3:
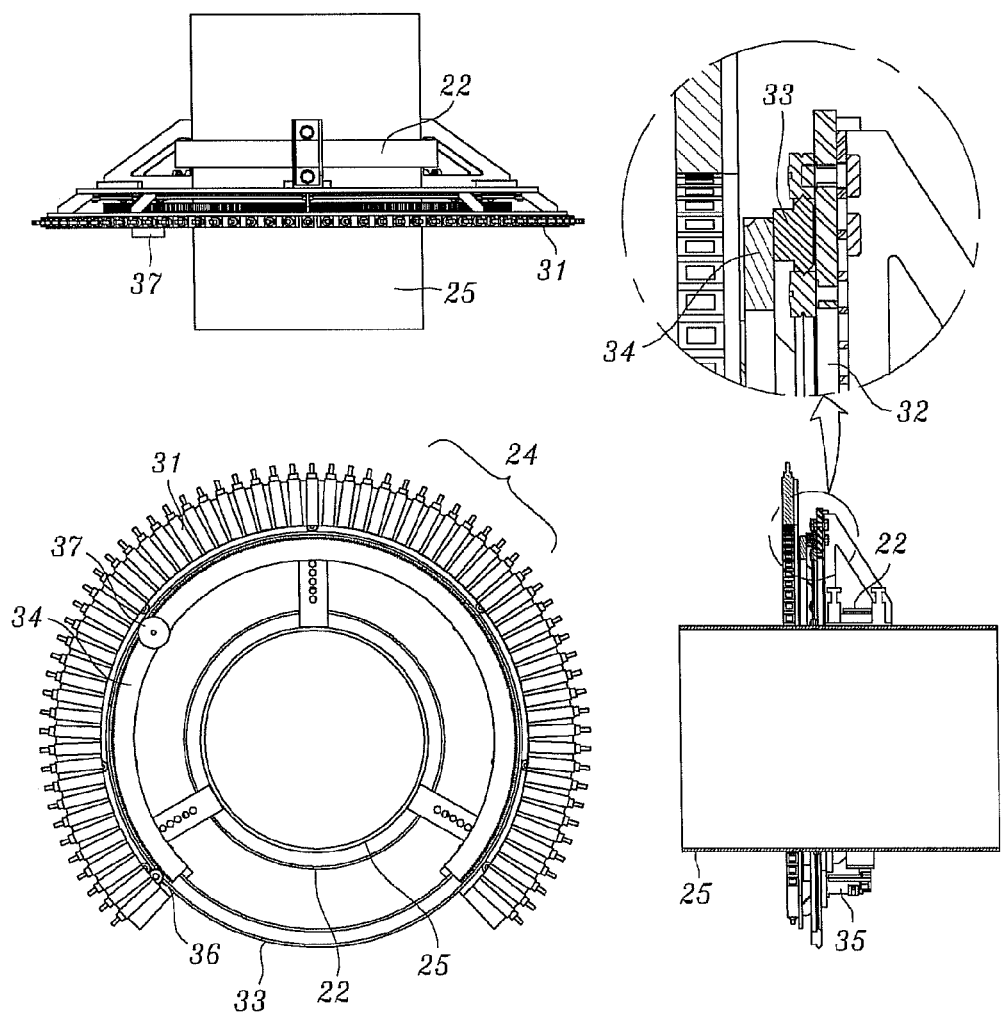
FIG. 3 shows the detailed configuration of the portable industrial limited angle gamma-ray tomography scanning system according to the exemplary embodiment of the present invention.

First, FIGS. 2 and 3 show the detailed configuration of the portable industrial limited angle gamma-ray tomography scanning system 20 according to the exemplary embodiment of the invention and will be described.

As shown in FIG. 2, the portable industrial limited angle gamma-ray tomography scanning system 20 according to the exemplary embodiment of the invention is generally made up of a scanning part 21 for tomography scanning, and a clamping part 22 for attaching the scanning part 21 to an object to be measured, and is attached to the outside of the object 25.

Here, the scanning part 21 for tomography scanning includes a source assembly generating radiation, driving device rotating the source assembly and a detector assembly 24 detecting the radiation generated from the source assembly.

The scanning part 21 has a structure in which the detector assembly 24 is fixed whereas the source assembly is displaced in order to reduce the measurement time.

In detail, as shown in FIG. 3, the detector assembly 24 is configured so that a plurality of detecting units 31 are arranged in a circular arc shape, and the source assembly is configured so that a source moving slide 33 and a source moving track 34 are disposed on a base plate 32 in turn, and that a source collimator 37 is displaced along the source moving track 34 by rotation of a motor 35 and a gear 36.

That is, as shown in FIG. 3, the gear 36 is engaged to teeth formed on a lateral face of the source moving track 34. Thus, when the motor 35 is driven to rotate the gear 36, the source collimator 37 is displaced along the source moving track 34 by the teeth formed on the lateral face of the source moving track 34.

Figure 4:
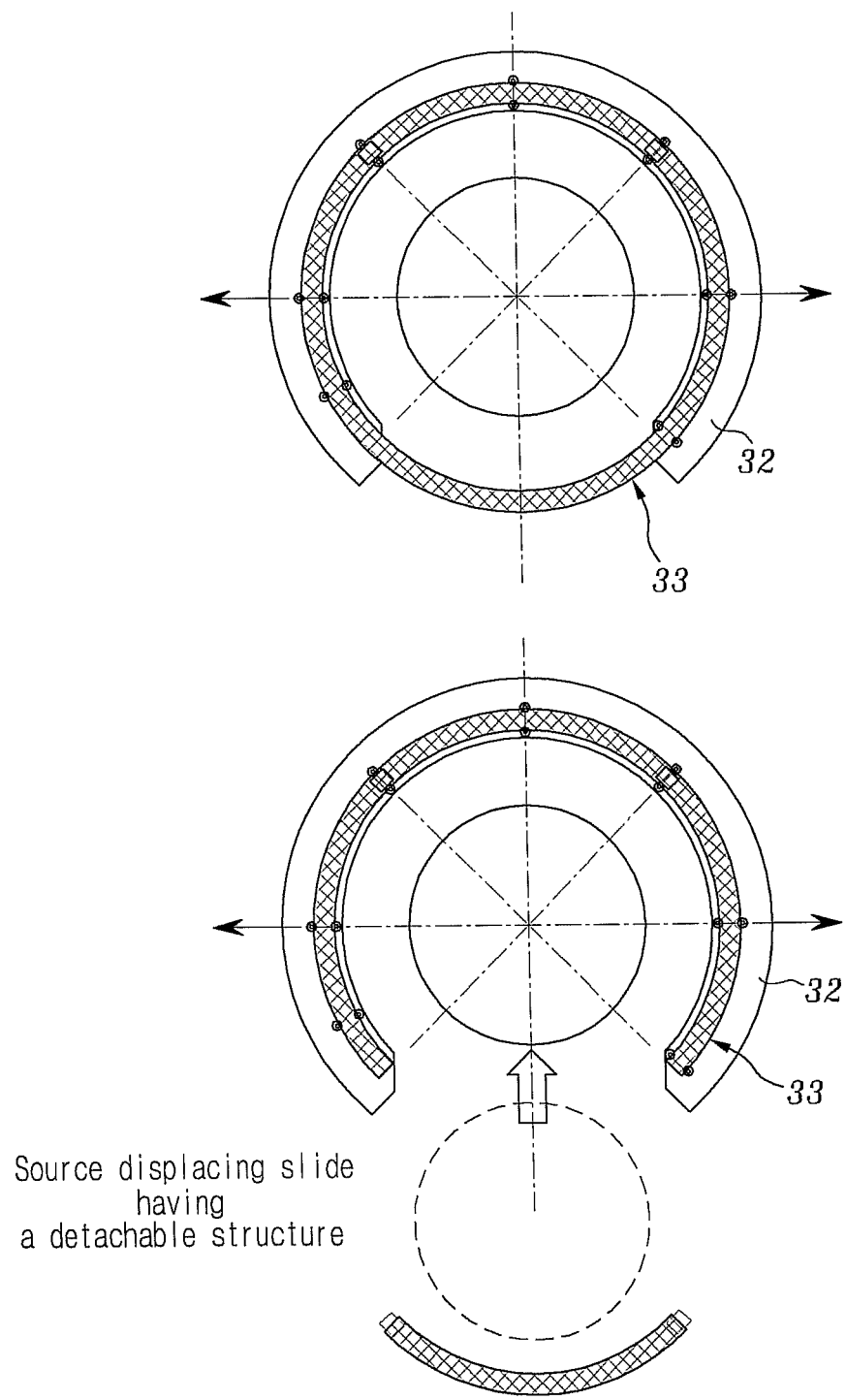
FIG. 4 shows the detailed configuration of a base plate and a source moving slide of the portable industrial limited angle gamma-ray tomography scanning system according to the exemplary embodiment of the present invention.

Further, as shown in FIG. 4, the source moving slide 33 coupled to the base plate 32 and may be formed in a detachable structure.

The plurality of detecting units 31 may be configured using, for instance, CsI gamma-ray detecting units.

Further, as the source assembly, a sealed gamma-ray source may be used. As a sealed radioactive isotope that emits gamma rays, $^{137}$Cs or $^{60}$Co may be used.

Moreover, the clamping part 22 is manufactured depending on a size of the object to be measured, and thus measurement is possible for objects of various sizes.

Subsequently, since data measured by the aforementioned configuration is a type where data of a specific range of angles is not present, cross-sectional reconstruction is performed using an image reconstruction program suitable for the cross-sectional reconstruction from this limited angle data.

Here, as an algorithm known to be good at the image reconstruction of limited angle data, one of iterative algorithm such as ML-EM, TV, or ART may be applied.

Thus, the configuration as described above allows the tomography scanning to be performed on an object to be scanned, such as a pipe or a cylinder, which is difficult to scan using an existing tomography scanner.

Next, the results from simulation and experiment using the portable industrial limited angle gamma-ray tomography scanning system according to the exemplary embodiment of the invention will be described with reference to FIGS. 5 and 6.

Figure 5:
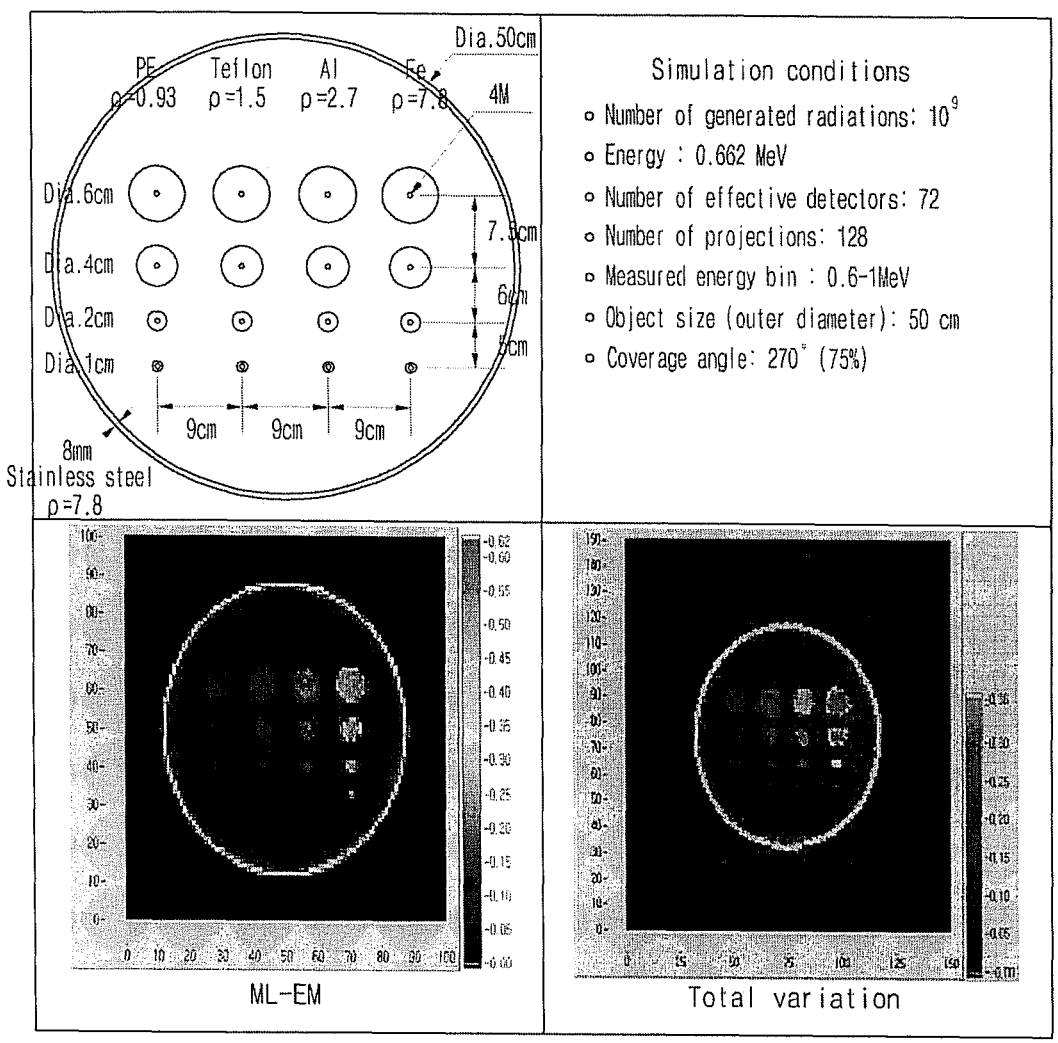
FIG. 5 shows the image reconstruction results from simulation data using the portable industrial limited angle gamma-ray tomography scanning system according to the exemplary embodiment of the present invention.

FIG. 5 show the results from simulation data using the portable industrial limited angle gamma-ray tomography scanning system according to the exemplary embodiment of the invention.

Figure 6:
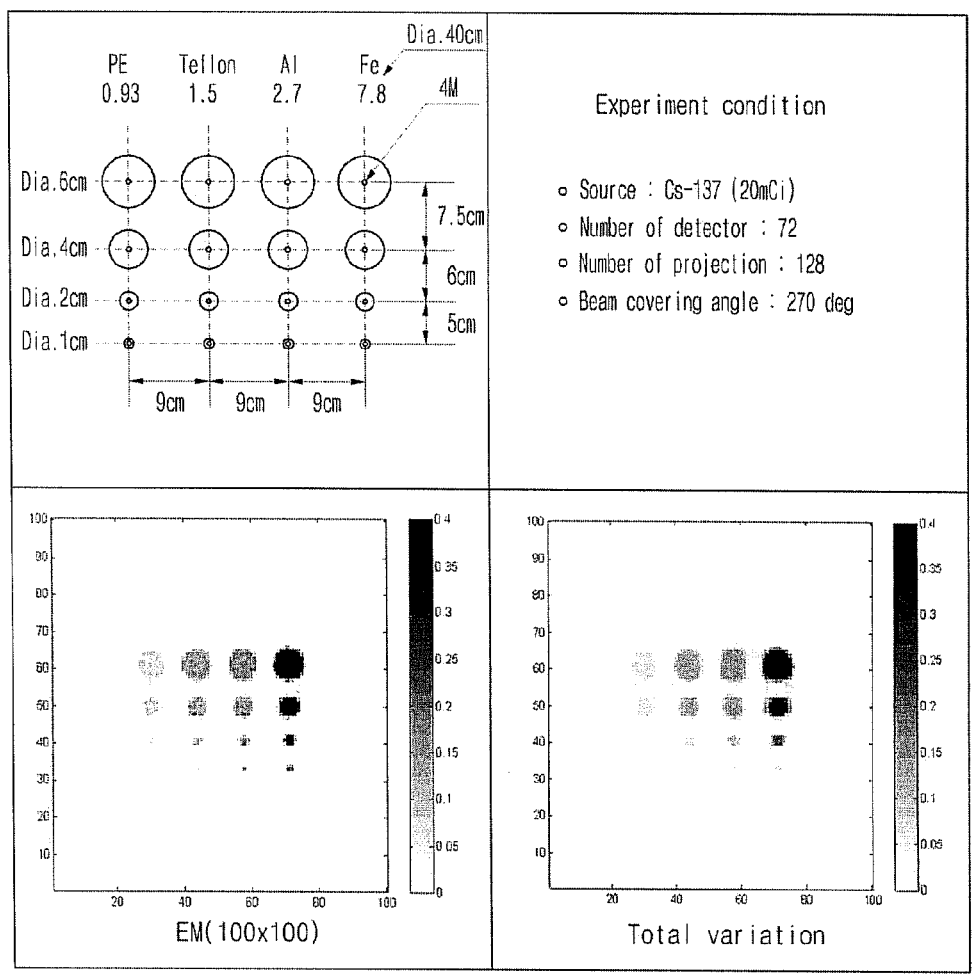
FIG. 6 shows the image reconstruction results from experimental data using the portable industrial limited angle gamma-ray tomography scanning system according to the exemplary embodiment of the present invention.

FIG. 6 show the results from experiment data using the portable industrial limited angle gamma-ray tomography scanning system according to the exemplary embodiment of the invention.

That is, the inventors of the present invention have verified feasibility of the proposed scanner as described above using a Monte Carlo computer simulation technique. At that time, the conditions of simulation were set as shown in FIG. 5.

Here, a rotation angle of the source relative to the detector is 270°, which is a value corresponding to 75% on the basis of 360°. As shown in FIGS. 5 and 6, it can be seen from the results from simulation and experiment that the shape of a phantom (i.e. an imaginary object) was successfully reconstructed without serious distortion.

As described above, the inventors of the present invention proved that the cross-sectional image of a pipe was successfully reconstructed using the portable industrial limited angle gamma-ray tomography scanning system according to the exemplary embodiment of the invention by means of the Monte Carlo computer simulation technique.

Subsequently, the detailed design for the portable industrial limited angle gamma-ray tomography scanning system as described above will be described with reference to FIGS. 7 and 8.

The portable industrial limited angle gamma-ray tomography scanning system according to the exemplary embodiment of the invention makes use of a small CsI detector, and includes an apparatus for tomography scanning and a clamping apparatus for attaching the tomography scanning apparatus to an object to be measured.

Figure 7:
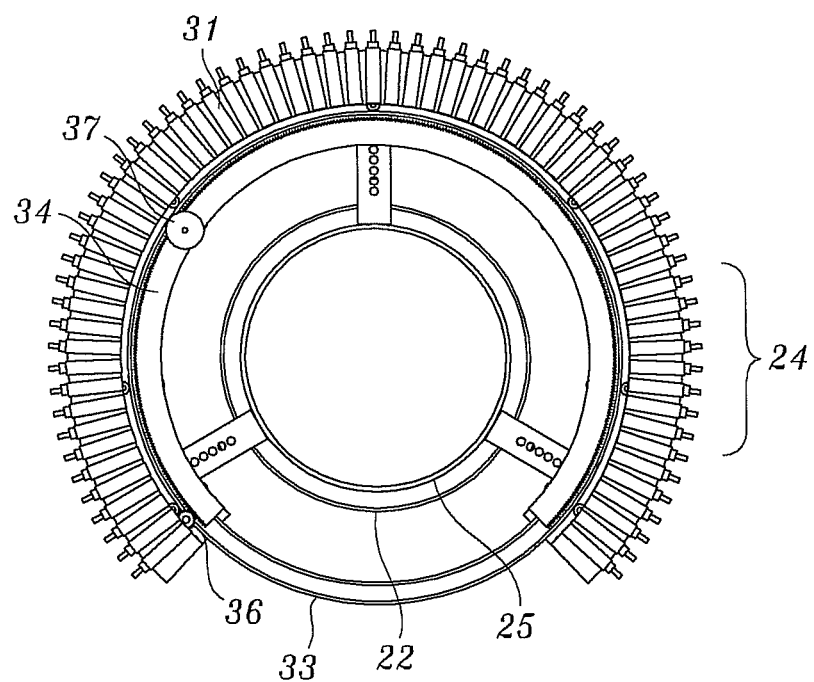
FIG. 7 is a diagram for explaining a detailed design for the portable industrial limited angle gamma-ray tomography scanning system according to the exemplary embodiment of the present invention.
Figure 7:
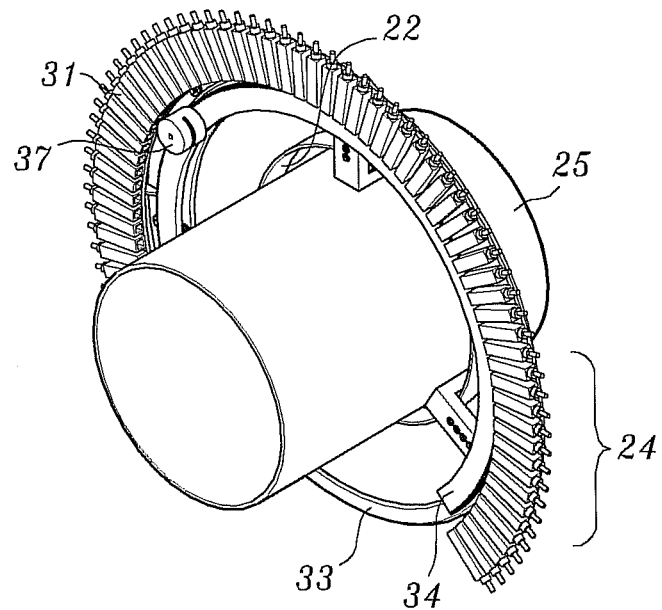
Figure 8:
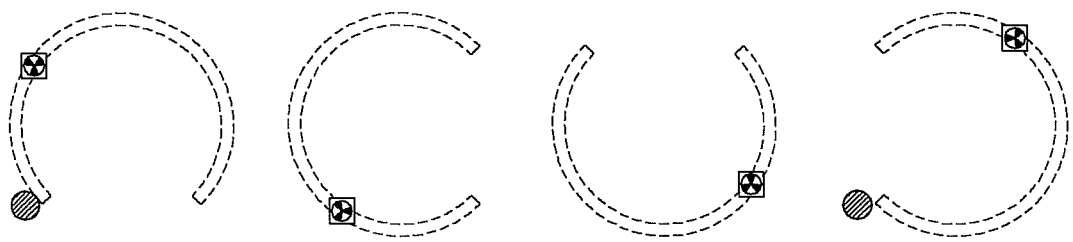
FIG. 8 shows a locus of the movement of a source of the portable industrial limited angle gamma-ray tomography scanning system according to the exemplary embodiment of the present invention.

In detail, as shown in FIGS. 7 and 8, the tomography scanning apparatus is configured to reduce the measurement time in such a manner that a detector assembly is fixed whereas a source assembly is displaced.

Here, a space for insertion around a pipe is required for direct attachment to the pipe in operation. To this end, radiation detecting units of the detector are configured to be uniformly arranged in a space excluding a portion for insertion around an object.

That is, as shown in FIG. 7, the overall arrangement of the radiation detecting units is similar to a C-shaped arrangement.

Further, the source assembly employs a sealed gamma-ray source.

As shown in FIGS. 7 and 8, the sealed gamma-ray source is movably attached to a C-shaped source moving slide located inside a circular arc of the C-shaped detector.

Here, as a radioactive isotope that emits gamma rays, $^{137}$Cs or $^{60}$Co may be used.

Further, the circular arc of the C-shaped detector and an open side of the C-shaped source moving slide for displacing the gamma-ray source are matched with each other in the same direction, are inserted around an object such as a pipe, and are attached to the clamping apparatus installed in advance by a base plate.

Figure 9:
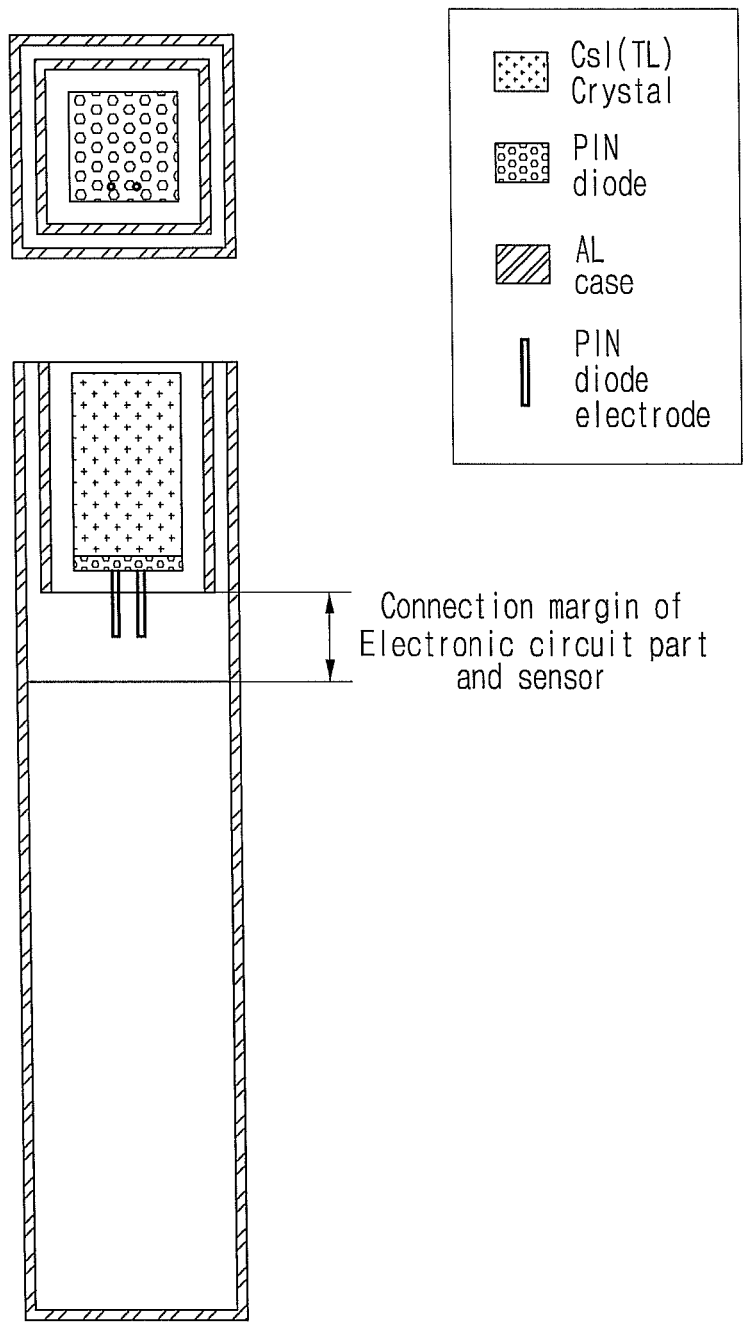
FIG. 9 schematically shows the detailed configuration of a detecting unit of the portable industrial limited angle gamma-ray tomography scanning system according to the exemplary embodiment of the present invention.

Here, a detector assembly for detecting gamma rays is configured, for instance, so that a plurality of CsI gamma-ray detecting units are arranged as shown in FIG. 9.

Figure 10:
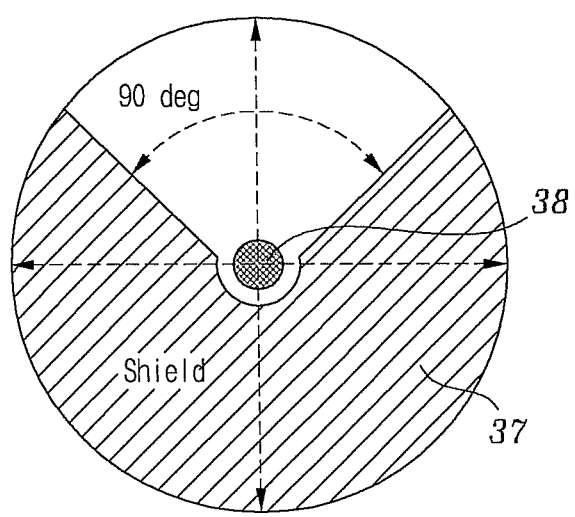
FIG. 10 is a diagram for explaining a source and its collimator of the portable industrial limited angle gamma-ray tomography scanning system according to the exemplary embodiment of the present invention.

FIG. 10 schematically shows the source and its collimator of the portable industrial limited angle gamma-ray tomography scanning system according to the exemplary embodiment of the invention.

As shown in FIG. 10, the source assembly includes a source collimator 37 and a source 38.

Here, the source 38 is located at the source collimator 37, and the source collimator 37 has a fan-shaped open face so as to allow radiation to be emitted only towards an object to be measured.

Figure 11:
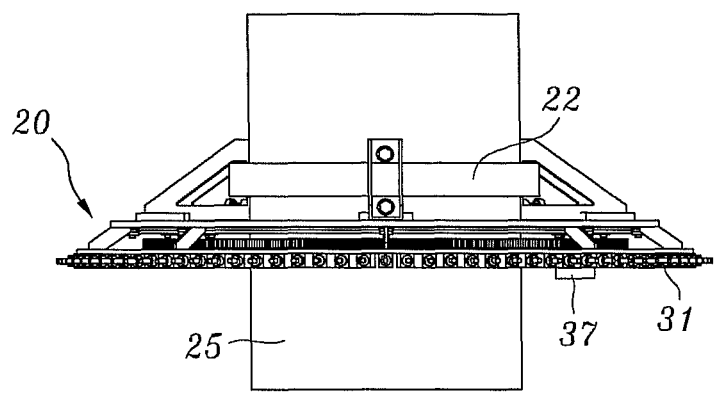
FIG. 11 schematically shows how the portable industrial limited angle gamma-ray tomography scanning system according to the exemplary embodiment of the present invention is installed on a pipe and performs measurement.
Figure 11:
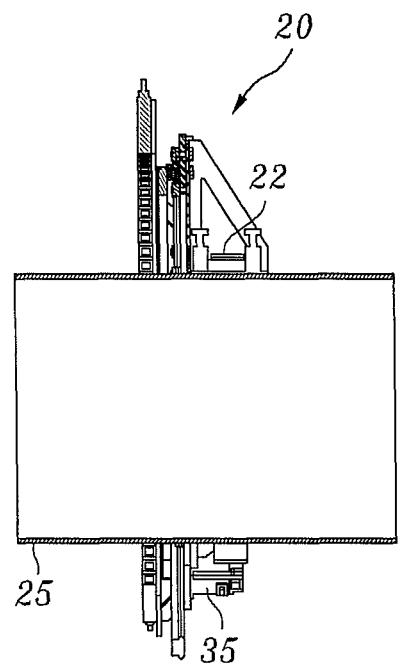

Thus, the portable industrial limited angle gamma-ray tomography scanning system configured as described above is attached to the pipe so as to perform measurement as shown in FIG. 11, so that it is possible to relieve the burden of separation, reassembly, etc. of the apparatus for attaching the tomography scanning system at a measurement position, to reduce the measurement time by miniaturizing the source assembly and displacing the source, and to be widely applied to the industrial field where the pipe and its equivalent need to be diagnosed because it is advantageous in constructing a portable system compared to the related art.

Although the exemplary embodiment of the present invention have been described for illustrative purposes, those skilled in the art will appreciate that various modifications, additions and substitutions are possible, without departing from the scope and spirit of the invention as disclosed in the accompanying claims.

What is claimed is:

1. A portable industrial limited angle gamma-ray tomography scanning system comprising:
    a scanning part for tomography scanning; and
    a clamping part for attaching the scanning part to an object to be measured,
    an image reconstructing part for performing cross-sectional reconstruction using an image reconstruction program to perform cross-sectional reconstruction of limited angle data on the basis of measured data,
    wherein the scanning part includes:
    a source assembly generating radiation of gamma-ray;
    a driving device rotating the source assembly; and
    a detector assembly detecting the radiation generated from the radiation source,
    and the source assembly includes:
    a source moving slide comprises two parts, a first part being disposed along a base plate having a C-shaped structure and a second part being detachable from the first part and filling an open part of the base plate;
    a source moving track that is coupled to the source moving slide; and
    a source collimator that is coupled to the source moving track,
    wherein said two parts of the source moving slide forms a closed circular structure.

2. The portable industrial limited angle gamma-ray tomography scanning system as set forth in claim 1, wherein the detector assembly is configured to be fixed, and the source assembly is configured to be displaced.

3. The portable industrial limited angle gamma-ray tomography scanning system as set forth in claim 1, wherein the source moving track includes teeth formed on a lateral face thereof so as to be engaged with the gear, whereby when the motor is driven to rotate the gear, the source collimator is displaced with the source moving track.

4. The portable industrial limited angle gamma-ray tomography scanning system as set forth in claim 1, wherein the source moving slide coupled to the base plate is configured to have a detachable structure.

5. The portable industrial limited angle gamma-ray tomography scanning system as set forth in claim 1, wherein the detector assembly is configured so that multiple detecting units are arranged in a circular arc shape.

6. The portable industrial limited angle gamma-ray tomography scanning system as set forth in claim 5, wherein the detecting unit employs a CsI gamma-ray detecting unit.

7. The portable industrial limited angle gamma-ray tomography scanning system as set forth in claim 1, wherein the source assembly employs a sealed gamma-ray source, and is configured to use $^{137}$Cs or $^{60}$Co as a radioactive isotope that emits gamma rays.

8. The portable industrial limited angle gamma-ray tomography scanning system as set forth in claim 1, wherein the clamping part is manufactured depending on a size of the object to be measured, whereby measurement is possible for objects of various sizes.

9. The portable industrial limited angle gamma-ray tomography scanning system as set forth in claim 1, wherein the image reconstruction program is configured to use an iterative algorithm such as a maximum likelihood-expectation maximization (ML-EM) algorithm, a total variation (TV) algorithm, or an algebraic reconstruction technique (ART) algorithm.

* * * * *